United States Patent [19]

Terada et al.

[11] Patent Number: 4,942,874
[45] Date of Patent: Jul. 24, 1990

[54] STEAM INHALER

[75] Inventors: Takao Terada, Higashiosaka; Toshiyuki Kobayashi, Kameoka, all of Japan

[73] Assignee: Omron Tateisi Electronics Co., Kyoto, Japan

[21] Appl. No.: 301,772

[22] Filed: Jan. 26, 1989

[30] Foreign Application Priority Data

Jan. 28, 1988 [JP] Japan .................. 63-9892[U]

[51] Int. Cl.$^5$ ............. A61M 11/00; A61M 16/16; A61M 16/18
[52] U.S. Cl. ............. 128/203.16; 128/203.17; 128/203.26; 128/200.21; 239/136; 239/370
[58] Field of Search ............. 128/200.14, 200.21, 128/203.12, 203.16, 203.17, 203.26, 203.27; 239/370, 136

[56] References Cited

U.S. PATENT DOCUMENTS

| 3,682,167 | 8/1972 | Urbanowica | 128/200.14 |
| 4,149,536 | 4/1979 | Villard | 128/200.14 |
| 4,318,397 | 3/1982 | Kobayashi | 128/200.21 |
| 4,604,999 | 8/1986 | Maeda | 128/200.21 |

FOREIGN PATENT DOCUMENTS 61-238249 10/1986 Japan ............. 128/200.21

Primary Examiner—Edgar S. Burr
Assistant Examiner—Kimberly L. Asher
Attorney, Agent, or Firm—Wegner & Bretschneider

[57] ABSTRACT

An improved steam inhaler for producing steam from water and aspirating inhalation liquid having a certain medical efficacy with the steam, comprising: a water supply tank, a first conduit, a first heating chamber, a second conduit, a second heating chamber, and a steam nozzle, along the path the water conveyed. The first and second heating chambers are provided with heating elements, and a one-way valve is provided in the first conduit. Therefore, the water boiled in the first chamber is conducted into the second heating chamber and prevented from returning to the water tank by the one-way valve. The water is completely vaporized in the second heating chamber. Since the water is thus metered from the water tank into the first heating chamber substantially upon demand, the steam inhaler can be activated immediately after the power is turned on, and can be deactivated immediately after the power is turned off. Thereby, the convenience of the steam inhaler is improved, and the waste of the inhalation liquid may be prevented.

9 Claims, 2 Drawing Sheets

STEAM INHALER

TECHNICAL FIELD

The present invention relates to a steam inhaler for vaporizing water into steam by heating it and, by using a jet of the steam thus produced, spraying a vapor or liquid for inhalation having a certain medical efficacy into the throat and other respiratory organs of the user, and in particular to such a steam inhaler which is highly convenient to use.

BACKGROUND OF THE INVENTION

As shown in FIG. 3, a conventional steam inhaler 41 typically comprises a case 42, an inhalation liquid tank 43, a water tank 45, a steam nozzle 46 and a heater 47. The inhalation tank 43 is detachably received in the case 42 to accommodate inhalation liquid F therein. An inhalation liquid tube 44a extends downwardly into the inhalation liquid tank 43. The upper end of the inhalation tube 44a is formed into an inhalation liquid nozzle 44. The steam nozzle 46 is attached to the inhalation liquid nozzle 44 so as to oppose the latter. The steam nozzle 46 is connected to an upper part of the water tank 45, whose bottom wall adjoins the heater 47 so that the water W in the water tank 45 may be heated. Numeral 48 denotes the cap of the water tank 45.

When electric current is supplied through the heater 47 causing it to be heated up, the water W in the water tank 45 is heated and turns into steam V. The steam V is discharged from the steam nozzle 46, and, owing to Bernoulli's principle, draws up the inhalation liquid F causing it to be discharged from the inhalation liquid nozzle 44. A mixture of the steam V and the inhalation liquid F is thus sprayed from the outlet 42a of the case 42.

In this conventional inhaler 41, the quantity of the water W contained in the water tank 45 is typically 30 to 70 milliliters, and two to three minutes is required before steam V is produced after starting the supply of electric current to the heater 47. If excessive amount of water is contained in the water tank 45, there is a chance that the water in the water tank 45 may be discharged from the steam nozzle 46 in liquid state.

If any water is still left in the water tank 45 when the power to the heater 47 is turned off, a considerable time interval may be required before the spraying stops, thereby causing a significant inconvenience to the user as well as some waste in the inhalation liquid.

BRIEF SUMMARY OF THE INVENTION

In view of such problems of the prior art, a primary object of the present invention is to provide an improved steam inhaler which becomes fully operative in a very short after the power is turned on.

A second object of the present invention is to provide an improved steam inhaler which stops being operative immediately after the power is turned off.

A third object of the present invention is to provide an improved steam inhaler which can accommodate more water and, therefore, stay operative longer than was possible heretofore for a given size of the inhaler.

These and other objects of the present invention can be accomplished by providing: a steam inhaler, comprising: a substantially enclosed water supply tank accommodating water therein; a first heating chamber of a relatively small capacity having a first heating element and at least partly located lower than a minimum water surface level of the water supply tank; a first conduit for conducting water from the water supply tank to the first heating chamber; a one-way valve provided in the first conduit to prevent the flow of water from the first heating chamber to the water supply tank; a second heating chamber of a relatively large capacity having a second heating element; a second conduit for communicating the first heating chamber with the second heating chamber; a steam nozzle for discharging the steam produced in the second heating chamber; and a pressure control passage communicating the second heating chamber with an upper part of the water supply tank.

According to this structure, the water in the water supply tank is introduced into the first heating chamber via the first conduit. The water is heated to boiling in the first heating chamber. The water is placed under pressure by the volumetric expansion of the water, and the boiling water, or the hot water, flows into the second heating chamber via the second conduit 16, but the hot water is prevented from returning to the water supply tank by means of the one-way valve. The hot water introduced into the second heating chamber is completely vaporized therein, and is discharged from the steam nozzle. Meanwhile, the second heating chamber and the upper part of the water supply tank are communicated with each other via the pressure control passage, and the water is smoothly supplied from the water supply tank to the first heating chamber due to the presence of a certain pressure in the water supply tank.

Since a small quantity of water is vaporized at a time in two steps, at first in the first heating chamber and then in the second heating chamber, the spraying of steam is started immediately after the electric power is turned on, and the water is completely vaporized without being discharged from the steam nozzle as liquid. Further, since the capacity of the first heating chamber is so small, the temperature therein drops rapidly and the spraying therefore stops in a short time after the power is turned off. Typically, a inhalation liquid nozzle communicating with the interior of an inhalation liquid tank is provided adjacent to the steam nozzle so as to cause a discharge of inhalation liquid from the inhalation liquid nozzle by means of negative pressure produced by a jet of the steam discharged from the steam nozzle.

According to a preferred embodiment of the present invention, the first heating chamber adjoins the bottom end of the water tank, and the first and second heating elements consist of a common planar heating element on which the first and second heating chambers are disposed. Since the first heating chamber is disposed in the immediate vicinity of the water tank, the first conduit contains very little water at any given moment, and this contributes to the rapid activation and deactivation of the steam inhaler according to the present invention. Further, this offers an advantage in improving the compactness of the layout.

According to another preferred embodiment of the present invention, the first heating chamber comprises a length of tube. Preferably, the second heating element consists of a planar heating element on which the second heating chamber is disposed, and the first heating element consists of a lateral extension of the second heating element, the tube being placed on the first heating element. This alternative arrangement can offer the same advantages as the aforementioned preferred embodiment.

BRIEF DESCRIPTION OF THE DRAWINGS

Now the present invention is described in the following with reference to the appended drawings, in which.

DETAILED DESCRIPTION OF THE PREFERRED EMBODIMENTS

Figure 1:
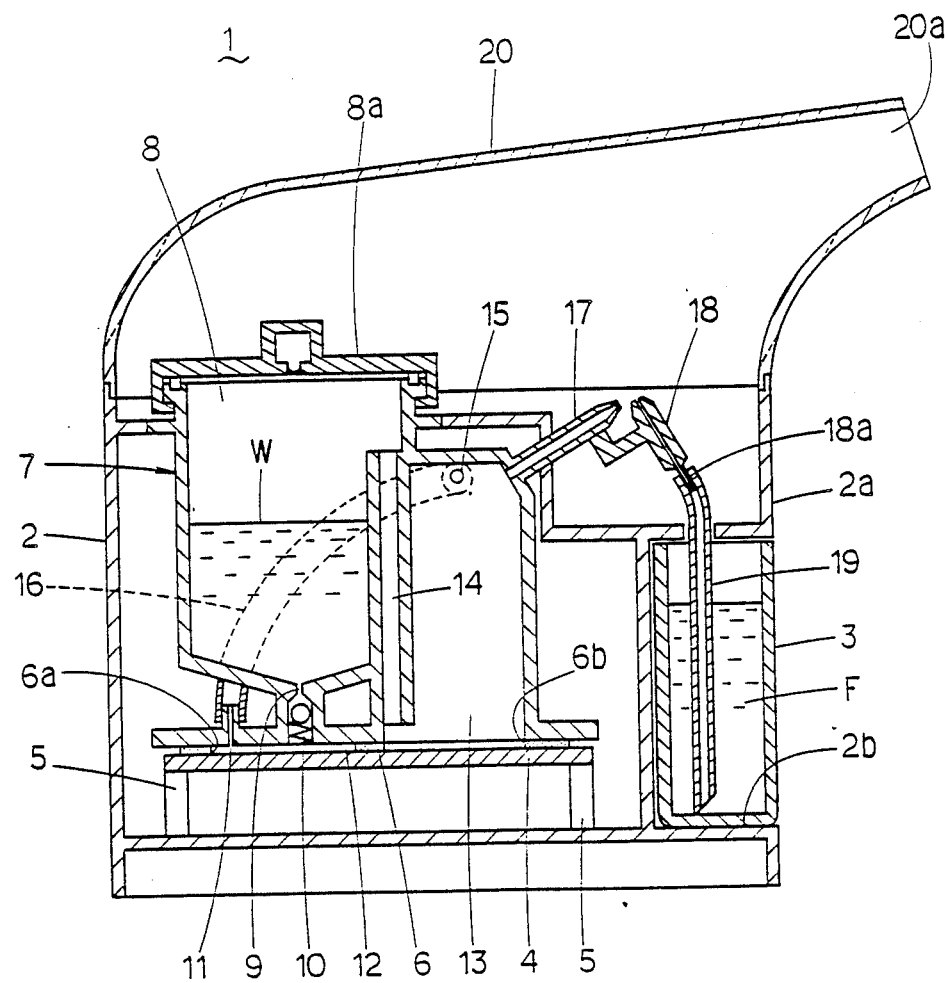
FIG. 1 is a sectional view of the first embodiment of the steam inhaler according to the present invention.

Referring to FIG. 1, the casing 2 of the steam inhaler 1 is provided with a cavity 2b in its front surface 2a, and this cavity 2b removably receives therein an inhalation liquid tank 3. To the bottom part of the casing 2 is attached a heater 4 consisting of a ceramic resistive heater 4 having a resistive value which increases with the increasing temperature and supported at the bottom of the casing 2 by spacers 5. On the heater 4 is placed a tank unit 7 with a planer gasket 6 interposed therebetween.

The gasket 6 is provided with a pair of cut-outs 6a and 6b. The tank unit 7 consists of a molded plastic member integrally formed with a water supply tank 8, a second heating chamber 13, and a pressure control tube (pressure control passage) 14. The water supply tank 8 is placed on the cut-out 6a in such a manner that a first heating chamber 12 of a small capacity may be defined by the upper surface of the heater 4, the bottom surface 7a of the tank unit 7, and the cut-out 6a of the gasket 6.

The water supply tank 8 and the first heating chamber 12 are communicated with each other via a first conduit 9. The first conduit 9 is provided with a one-way valve 10 to prevent the flow of the hot water from the first heating chamber 12 to the water supply tank 8.

The bottom end of the second heating chamber 13 is defined by the upper surface of the heater 4 exposed through the second cut-out 6b of the gasket 6. The bottom portion of the second heating chamber 13 and the upper part of the water supply tank 8 are communicated with each other via the pressure control tube (pressure control passage) 14. The water filling inlet at the top of the water supply tank 8 is provided with a detachable cap 8a.

The first heating chamber 12 is provided with a hot water outlet 11. The upper part of the second heating chamber 13 is provided with a hot water inlet 15 at a part located above the level of the water surface of the water supply tank 8. The hot water outlet 11 and the hot water inlet 15 are communicated with each other by a second conduit 16 consisting of a tube having a steam resistant property.

A steam nozzle 17 projects from an upper part of the second heating chamber 13. To the free end of the steam nozzle 17 is attached an inhalation liquid nozzle 18. The lower end 18a of the inhalation liquid nozzle 18 is fitted into an inhalation liquid tube 19 which extends downwardly into the inhalation liquid tank 3.

The upper part of the casing 2 is closed by a cover 20 having a spray outlet 20a for conducting and directing the spray of the mixture of the inhalation liquid and the steam from the steam nozzle 17 and the inhalation liquid nozzle 18 in a prescribed direction.

Now the operation of the inhaler 1 of the present embodiment is described in the following.

First of all, the cover 20 and the cap 8a are removed, and water W is poured into the water supply tank 8 to a prescribed level. At this time point, some of the water flows into the first heating chamber 12 and a part of the second conduit 16 to the extent where the water surface of the second conduit 16 agrees with the water surface of the water supply tank 8. Meanwhile, the inhalation liquid tank 3 is also removed from the main body casing 2, and is filled with inhalation liquid F having a medical efficacy.

Then, the cap 8a is placed on the water supply tank 8 and the cover 20 is placed on the main body casing 2. At the same time, the inhalation liquid tank 3 is attached to the main body casing 2 and the power switch not shown in the drawing is turned on to supply electric current to the heater 4.

As the heater 4 is heated up, the water in the first heating chamber 12 is heated to boiling and increases its volume by producing steam. The hot water containing steam cannot flow back to the water supply tank 8 due to the presence of the one-way valve 10, but drips into the second heating chamber 13 via the second conduit 16 and the hot water inlet 15.

The hot water which has dripped into the second heating chamber 13 is completely vaporized on the surface of the heater 4. This steam is discharged from the steam nozzle 17 and, owing to Bernoulli's principle, draws the inhalation liquid F from the inhalation liquid tube 19 to be sprayed outwardly from the spray outlet 20a of the cover 20.

As the quantity of the hot water in the first heating chamber 12 diminishes by dripping into the second heating chamber 13, a corresponding amount of water is supplied from the water supply tank 8 to the first heating chamber 12. At this time point, since the upper part of the water supply tank 8 and the second heating chamber 13 are communicated with each other via the pressure control conduit 14, the pressure transmitted from the second heating chamber 13 to the upper part of the water supply tank 8 causes the water to be smoothly supplied to the first heating chamber 12.

Figure 2:
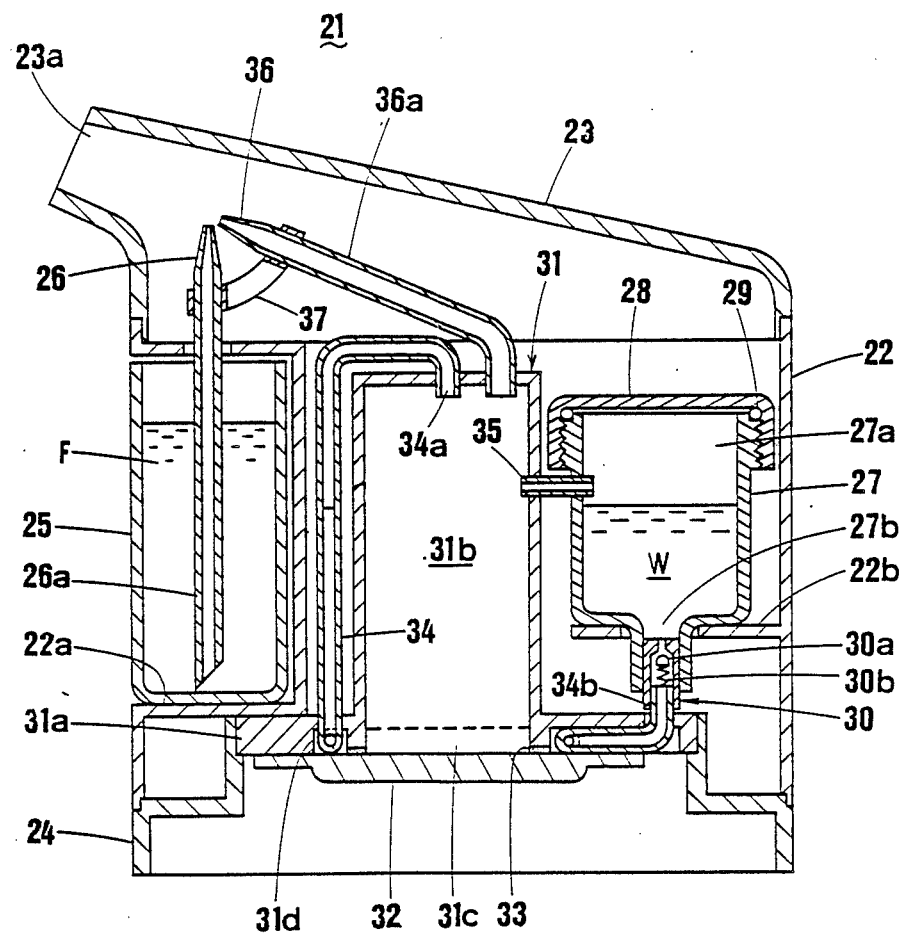
FIG. 2 is a sectional view similar to FIG. 1 showing the second embodiment of the present invention.
Figure 3:
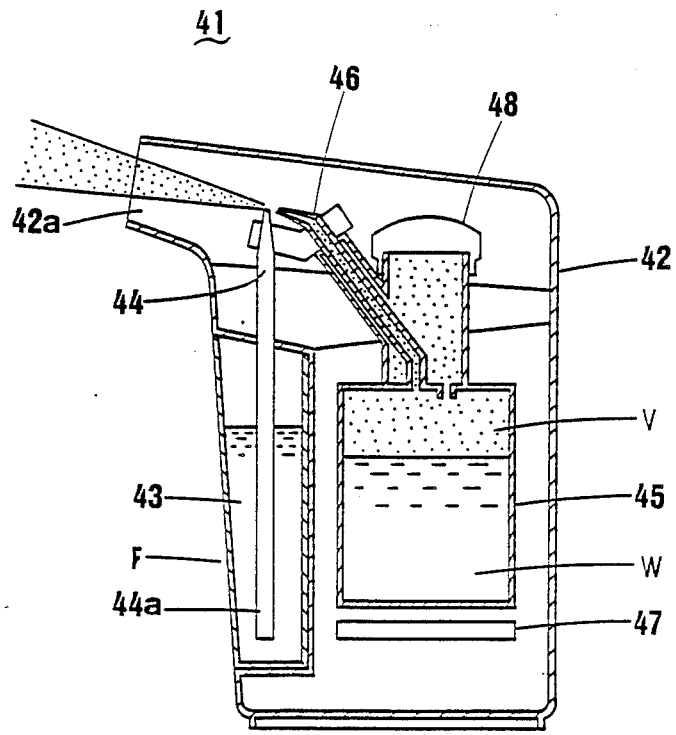
FIG. 3 is a sectional view of a conventional steam inhaler.

FIG. 2 shows the second embodiment of steam inhaler according to the present invention. This steam inhaler 21 comprises a casing 22, and a cover 23 closing the upper part of the casing 22 and provided with a spray outlet 23a. The bottom part of the casing 22 is provided with a base 24. The front face of the casing 22 is provided with a cavity 22a for receiving an inhalation liquid tank 25 therein. The inhalation liquid tank 25 accommodates inhalation liquid F having a certain medical efficacy. An inhalation liquid tube 26a descends into the inhalation liquid tank 25 and the upper end of the inhalation liquid tube 26a which is formed into an inhalation liquid nozzle 26 is supported, via a bracket 37, by a steam nozzle 36 which is described hereinafter.

The casing 22 is internally provided with a water supply tank 27 and a heating tank 31. The water supply tank 27 is supported by a rib 22b projecting from the inner side wall of the casing 22, and the upper opening 27a of the water supply tank 27 is closed air-tight by a detachable cap 28 equipped with a seal ring 29.

A lower central opening 27b in the water supply tank 27 is provided with a one-way valve 30 which consists of a ball 30a and a coil spring 30b upwardly urging the ball against a valve seat. The one-way valve 30 permits the flow of water from the water supply tank 27 unless the ball 30a is pressed against the valve seat by a certain pressure developed across the one-way valve 30.

A heating chamber 31b is defined by the cylindrical heating tank 31 comprising an enclosed top, an open bottom 31c closed by a surface of a planer heater 32 attached to the bottom end of the heating tank 31 by way of a gasket 33, and a radial flange 31a at its bottom end. The bottom end surface of the flange 31a is provided with an arcuate groove 31d which circumferentially extends over a certain angle. This groove 31d opposes the peripheral part of the heater 32. A conduit 34 connected to the bottom end of the water supply tank 27 or the one-way valve 30 is passed through this groove 31d, and extends upwardly along the side wall of the heating tank 31 before it is finally communicated with the upper part of the heating chamber 31b at a point which is higher than the normal level of the water surface in the water supply tank 27.

The heating chamber 31b and an upper part of the water supply tank 27 are communicated with each other via a communication passage 35. Further, the steam nozzle tube 36a projects from the upper end of the heating tank 31 and its free end is formed into the steam nozzle 36.

Now the operation of the second embodiment of the steam inhaler according to the present invention is described in the following.

First of all, inhalation liquid F is filled into the inhalation liquid tank 25, and water is filled into the water supply tank 27 by removing the cap 28. The water flows into the conduit 34 through the one-way valve 30 until the water surface level in the conduit 34 agrees with the water surface level of the water supply tank 27.

After the cap 28 is closed and electric power is supplied to the heater 32, the water in the conduit 34 boils due to the heat transmitted thereto from the heater 32, and increases its volume due to the generation of steam. The resulting increase in the pressure in the conduit 34 closes the one-way valve 30, and the heated water Comes to drip from the end of the conduit 34a connected to the heating chamber 31.

The water is completely vaporized in the heating chamber 31b by the heat from the heater 32. The produced steam is led out of the heating chamber 31b through the steam nozzle tube 36a, and is discharged from the steam nozzle 36a. This jet of steam draws the inhalation liquid F from the inhalation liquid tube 36a owing to Bernoulli's principle, and sprays it out of the spray nozzle 23a. According to this embodiment, it takes less than one-minute after the power is turned on before steam is produced from the steam nozzle.

Meanwhile, the volume of the water in the conduit 34 is reduced by the dripping of the water into the heating chamber 31b, and this causes a reduction in the pressure in the conduit 34 to a sufficient extent to open the one-way valve 30. As a result, an appropriate amount of water is introduced into the conduit 34, and the above described process is repeated until the power to the heater 32 is turned off.

According to the above described embodiments, the first heating chamber 12 and the second heating chamber 13 or the conduit 34 and the heating chamber 31b were heated by the same heater or heating means 4 or 32, but separate heating elements may be provided to the two parts that are required to be heated, as shown in the drawing figures among other possible design variations. I.e., each heater 4 and 32, may be composed of separate heating elements 4-4', and 32-32', respectively.

The configurations and arrangements of the first heating chamber, the second heating chamber, and other parts of the inhaler are not limited by the above described embodiments, but may be appropriately modified.

As described above, the inhaler of the present invention has the advantage that the spraying is started in a short time after the power is turned on. The inhaler of the present invention has the additional advantage that the spraying stops immediately after the power is turned off. Further, according to the inhaler of the present invention, there is provided the additional advantage that the hot water is prevented from being discharged from the steam nozzle even when an excessive amount of water is filled into the water supply tank.

What we claim is:

1. A steam inhaler, comprising:
   a water supply tank accommodating water therein;
   a first heating chamber of a relatively small capacity and at least partly located lower than a minimum water surface level of said water supply tank;
   a first conduit for conducting water from said water supply tank to said first heating chamber;
   a one-way valve provided in said first conduit to prevent the flow of water from said first heating chamber to said water supply tank;
   a second heating chamber of a relatively large capacity;
   a heating means for heating said first heating chamber and said second heating chamber;
   a second conduit for communicating said first heating chamber with said second heating chamber;
   a steam nozzle for discharging the steam produced in the second heating chamber; and
   a pressure control passage communicating said second heating chamber with an upper part of said water supply tank.

2. A steam inhaler as defined in claim 1, wherein a inhalation liquid nozzle communicating with the interior of an inhalation liquid tank is provided adjacent to said steam nozzle so as to cause a discharge of inhalation liquid from said inhalation liquid nozzle by means of negative pressure produced by steam discharged from said steam nozzle.

3. A steam inhaler as defined in claim 1, wherein said first heating chamber adjoins the bottom end of said water supply tank.

4. A steam inhaler as defined in claim 3, wherein said first and second heating elements consist of a common planar heating element on which said first and second heating chambers are disposed.

5. A steam inhaler as defined in claim 1, wherein said heating means includes first and second heating elements.

6. A steam inhaler, comprising:
   a water supply tank accommodating water therein;
   a first heating chamber of a relatively small capacity and at least partly located lower than a minimum water surface level of said water supply tank;
   a first conduit for conducting water from said water supply tank to said first heating chamber;
   a one-way valve provided in said first conduit to prevent the flow of water from said first heating chamber to said water supply tank;
   a second heating chamber of a relatively large capacity, said second heating chamber communicating with said first heating chamber;

a heating means for heating said first heating chamber and said second heating chamber;

a steam nozzle for discharging the steam produced in said second heating chamber; and a passage communicating said second heating chamber with an upper part of said water supply tank.

7. A steam inhaler as defined in claim 6, wherein said heating means includes first and second heating elements.

8. A steam inhaler as defined in claim 7, wherein said first heating chamber comprises a length of tube.

9. A steam inhaler as defined in claim 8, wherein said second heating element consists of a planar heating element on which said second heating chamber is disposed, and said first heating element consists of a lateral extension of said second heating element, said tube being placed on said first heating element.

* * * * *